United States Patent [19]
MacKenzie et al.

[11] Patent Number: 6,034,082
[45] Date of Patent: Mar. 7, 2000

[54] 5-AZABICYCLO(3.1.0)HEXYLALKYL-2-PIPERIODONES AND —GLUTARIMIDES AS NEUROKININ RECEPTOR ANTAGONISTS

[75] Inventors: Alexander Roderick MacKenzie; Allan Patrick Marchington; Donald Stuart Middleton; Sandra Dora Meadows, all of Sandwich, United Kingdom

[73] Assignee: Pfizer Inc., New York, N.Y.

[21] Appl. No.: 09/074,931

[22] PCT Filed: Nov. 11, 1996

[86] PCT No.: PCT/EP96/05000

§ 371 Date: May 15, 1998

§ 102(e) Date: May 15, 1998

[87] PCT Pub. No.: WO97/19942

PCT Pub. Date: Jun. 5, 1997

[30] Foreign Application Priority Data

Nov. 25, 1995 [GB] United Kingdom .................. 9524157

[51] Int. Cl.$^7$ ...................... A61K 31/535; A61K 31/445; C07D 401/02; C07D 413/14; C07D 243/08
[52] U.S. Cl. ...................... 514/233.5; 514/211; 514/212; 514/218; 514/253; 514/316; 514/323; 540/544; 540/575; 540/597; 544/130; 544/364; 546/187; 546/200
[58] Field of Search ...................... 514/211, 212, 514/218, 233.5, 253, 316, 323; 540/544, 575, 597; 544/130, 364; 546/187, 200

[56] References Cited

FOREIGN PATENT DOCUMENTS 0512901 11/1992 European Pat. Off. .
WO 9605193 2/1996 WIPO .

*Primary Examiner*—Mukund J. Shah
*Assistant Examiner*—Brenda Coleman
*Attorney, Agent, or Firm*—Peter C. Richardson; Paul H. Ginsburg

[57] ABSTRACT

Compounds of formula (I)

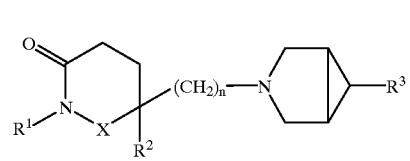

and salts thereof, wherein: $R^1$ is $C_1-C_6$ alkyl, $C_3-C_7$ cycloalkyl, $C_3-C_7$ cycloalkyl($C_1-C_4$)alky aryl or aryl ($C_1-C_4$)alkyl; wherein the $C_1-C_6$alkyl group is optionally substituted by fluorine and the $C_3-C_7$cycloalkyl or $C_3-C_7$cycloalkyl($C_1-C_4$)alkyl group is optionally substituted in the cycloalkyl ring by up to two substituents each independently selected from halo, $C_1-C_4$alkoxy or halo ($C_1-C_4$)alkoxy; $R^2$ is phenyl optionally substituted with one or two halo substituents or is indolyl, thienyl, benzothienyl or naphthyl; $R^3$ is $NH_2$, —$NR^4SO_2(C_1-C_6alkyl)$, —$NR^4SO_2$ aryl, —$NR^4SO_2N(R^4)_2$, $NR^4CO(C_1-C_6alkyl)$, —$NR^4CO$ aryl or a group or formula (a)

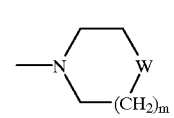

wherein W is O, $NR^5$, CH(OH), $CHCO_2H$, $CHN(R^4)_2$, CHF, $CF_2$, C=O or $CH_2$; $R^4$ is H or $C_1-C_6$ alkyl; $R^5$ is H, $C_1-C_6$ alkyl, $C_3-C_7$cycloalkyl, $C_3-C_7$cycloalkyl($C_1-C_6$)alkyl, $C_2-C_6$alkanoyl, $C_4-C_8$cycloalkanoly, $C_3-C_7$cycloalkyl ($C_2-C_6$)alkanoyl, aryl CO—, $C_1-C_6$alkylSO$_2$—, ($R^4$)$_2$NSO$_2$—, $C_3-C_7$cycloalkylSO$_2$—, $C_3-C_7$cycloalkyl ($C_1-C_6$)alkyl-SO$_2$—, or arylSO$_2$—; X is $CH_2$ or C=O; m is 0, 1 or 2 with the proviso that m is not O when W is $NR^5$, C=O, or O; and n is an integer of from 1 to 4. These compounds are neurokinin receptor antagonists of utility in the treatment of a variety of medical conditions including urinary incontinence, asthma and related conditions.

8 Claims, No Drawings

5-AZABICYCLO(3.1.0)HEXYLALKYL-2-PIPERIODONES AND — GLUTARIMIDES AS NEUROKININ RECEPTOR ANTAGONISTS

This is a 371 National Stage filing of PCT/EP96/05000, filed Nov. 11, 1996.

BACKGROUND OF THE INVENTION

This invention relates to piperidone derivatives which are neurokinin receptor antagonists of utility in the treatment of a variety of medical conditions including, for example, urinary incontinence, asthma and related conditions. More particularly this invention relates to certain 5-aryl-5-(azabicyclo[3.1.0]hexane alkyl)-N-substituted-piperidone derivatives, to processes for their preparation, compositions thereof and their use in medicine.

According to the specification of our co-pending International patent application WO 96/05193 we describe and claim a series of 5-aryl-5-azetidinylalkyl-piperidone derivatives. The compounds are antagonists of tachykinins, including neurokinin A, neurokinin B and Substance P, acting at the human neurokinin-1 ($NK_1$), neurokinin-2 ($NK_2$) or neurokinin-3 ($NK_3$) receptor, and are therefore potentially useful for preventing or treating a variety of medical conditions in which these receptors have been implicated, including inflammatory diseases such as arthritis, psoriasis, asthma or inflammatory bowel disease; central nervous system disorders such as anxiety, depression, dementia or psychosis; gastro-intestinal disorders such as functional bowel disease, irritable bowel syndrome, gastro-oesophageal reflux, faceal incontinence, colitis, Crohn's disease or diseases caused by *Helicobacter pylori* or other bacteria; urogenital tract disorders such as incontinence, hyperreflexia, impotence or cystitis; pulmonary disorders such as chronic obstructive airways disease; allergies such as eczma, contact dermatitis, atopic dermatitis, urticaria, rhinitis or hypersensitivity disorders such as to poison ivy; vasospastic diseases such as angina or Reynaud's disease; proliferative disorders such as cancer or a disorder involving fibroblast proliferation; fibrosing or collagen diseases such as scleroderma or eosinophillic fascioliasis; reflux sympathetic dystrophy such as shoulder/hand syndrome; addiction disorders such as alcoholism; stress-related somatic disorders; peripheral neuropathies such as diabetic neuropathy, neuralgia, causalgia, painful neuropathy, burns, herpetic neuralgia or post herpetic neuralgia; neuropathological disorders such as Alzheimer's disease or multiple sclerosis, disorders related to immune enhancement or suppression such as systemic lupus erythematosis; rheumatic diseases such as fibrositis or emesis; opthalmic diseases such as retinopathy; viral diseases such as colds and influenza; cough; acute or chronic pain or migraine.

The present invention provides a further series of related compounds wherein the piperidone-5-substituent is an azabicyclo[3.1.0]hexanealkyl-group. Also claimed are the corresponding di-one (glutarimide) derivatives. The compounds are potent and selective antagonists of tachykinins including neurokinin A, neurokinin B and substance P, active at the human $NK_1$, $NK_2$ and $NK_3$ receptors and they thus have potential utility in any of the disease states indicated above including, in particular treating or preventing inflammatory diseases such as arthritis, psoriasis, asthma or inflammatory bowel disease; central nervous system disorders such as anxiety, depression, dementia or psychosis; gastrointestinal disorders such as functional bowel disease, irritable bowel syndrome, gastro-oesophageal reflux, faecal incontinence, colitis or Crohn's disease; urogenital tract disorders such as incontinence or cystisis; pulmonary disorders such as chronic obstructive airways disease; allergies such as eczema, contact dermatitis or rhinitis; hypersensitivity disorders such as to poison ivy; peripheral neuropathies such as diabetic neuropathy, neuralgia, causalgia, painful neuropathy, burns, herpetic neuralgia or post-herpetic neuralgia; cough or acute or chronic pain.

SUMMARY OF THE INVENTION

Thus, the present invention provides compounds having the formula:

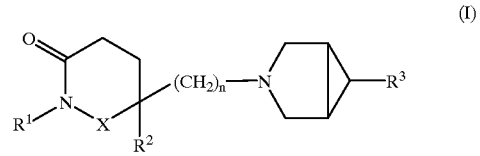

(I)

and pharmaceutically acceptable salts thereof, wherein:

$R^1$ is $C_1$–$C_6$ alkyl, $C_3$–$C_7$ cycloalkyl, $C_3$–$C_7$ cycloalkyl ($C_1$–$C_4$)alkyl, aryl or aryl-($C_1$–$C_4$)alkyl; wherein the $C_1$–$C_6$ alkyl group is optionally substituted by one or more fluorine atoms and the $C_3$–$C_7$ cycloalkyl or $C_3$–$C_7$ cycloalkyl ($C_1$–$C_4$)alkyl group is optionally substituted in the cycloalkyl ring by up to two substituents each independently selected from halo, $C_1$–$C_4$ alkoxy or halo($C_1$–$C_4$)alkoxy;

$R^2$ is phenyl optionally substituted with one or two halo substituents or is indolyl, thienyl, benzothienyl or naphthyl;

$R^3$ is $NH_2$, —$NR^4SO_2(C_1$–$C_6$alkyl), —$NR^4SO_2$aryl, —$NR^4SO_2N(R^4)_2$, —$NR^4CO(C_1$–$C_6$ alkyl), —$NR^4CO$ aryl or a group of the formula:

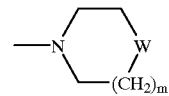

wherein W is O, $NR^5$, CH(OH), $CHCO_2H$, $CHN(R^4)_2$, CHF, $CF_2$, C=O or $CH_2$;

$R^4$ is H or $C_1$–$C_6$ alkyl;

$R^5$ is H, $C_1$–$C_6$alkyl, $C_3$–$C_7$cycloalkyl, $C_3$–$C_7$ cycloalkyl ($C_1$–$C_6$)alkyl, $C_2$–$C_6$ alkanoyl, $C_4$–$C_8$ cycloalkanoyl, $C_3$–$C_7$ cycloalkyl($C_2$–$C_6$)alkanoyl, aryl CO—, $C_1$–$C_6$alkyl $SO_2$—, $(R^4)_2NSO_2$—, $C_3$–$C_7$cycloalkyl $SO_2$—, $C_3$–$C_7$ cycloalkyl-($C_1$–$C_6$)alkyl $SO_2$— or aryl$SO_2$—;

X is $CH_2$ or C=O;

m is 0, 1 or 2 with the proviso that m is not 0 when W is $NR^5$, C=O, or O; and n is an integer of from 1 to 4.

In the above definitions of $R^1$, $R^3$ and $R^5$, aryl means phenyl optionally substituted by halo, $C_1$–$C_4$ alkyl, $C_1$–$C_4$alkoxy, halo($C_1$–$C_4$)alkyl or halo($C_1$–$C_4$)alkoxy, and halo means fluoro, chloro, bromo or iodo. Alkyl and alkoxy groups containing three or more carbon atoms may be straight or branched-chain.

The pharmaceutically acceptable salts of the compounds of the formula (I) include the acid addition and the base salts thereof. Suitable acid addition salts are formed from acids which form non-toxic salts; examples are the hydrochloride, hydrobromide, hydrolodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts. Suitable base salts are formed from bases which form non-toxic salts; examples are the aluminium, calcium, lithium, magnesium, potassium, sodium, zinc and diethanolamine salts.

The compounds of the formula (I) may contain one or more asymmetric carbon atoms and may therefore exist in two or more stereoisomeric forms. The present invention includes the individual stereoisomers of the compounds of the formula (I) and mixtures thereof. Separation of diastereoisomers may be achieved by conventional techniques, e.g. by fractional crystallisation or chromatography of a stereoisomeric mixture of a compound of the formula (I) or a suitable salt or derivative thereof.

Preferred examples of the compounds of the formula (I) are those wherein X is $CH_2$, $R^1$ is cyclopropylmethyl or benzyl; $R^2$ is 3,4-dichlorophenyl, n is 2 and $R^3$ is morpholino, methanesulphonylamino, pentafluorophenylsulphonyl, fluorophenylsulphonyl, or fluorophenylcarboxamido.

The preferred compounds of the formula (I) and salts thereof where n is 2 have the (S)-stereochemistry at the position of attachment of the alkylene and $R^2$ groups to the pyridone ring.

Particular and preferred examples of compounds of the invention include: 5(S)-5-(3,4-dichlorophenyl)-1-(cyclopropylmethyl)-5-(2-[1α,5α,6α,6-morpholino-3-azabicyclo[3.1.0]hexane]ethyl)-2-piperidone.

DETAILED DESCRIPTION OF THE INVENTION

The compounds of the formula (I) provided by this invention can be prepared by reductive amination using as starting materials a compound of the formula:

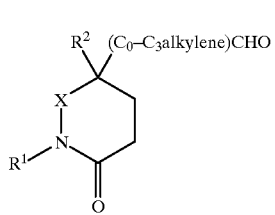

(II)

where $R^1$, $R^2$ and X are as previously defined for a compound of the formula (I), and a compound of the formula:

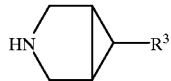

(III)

or an acid addition salt thereof, where $R^3$ is as previously defined for a compound of the formula (I). The reaction is preferably carried out in the presence of a suitable acid, e.g. acetic acid.

The reaction proceeds via the initial formation of an intermediate iminium salt of the formula:

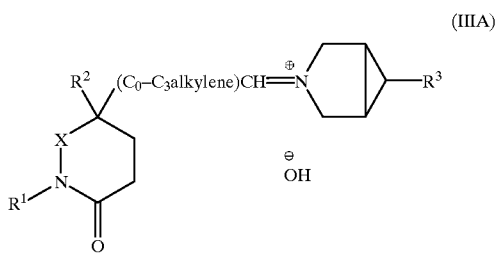

(IIIA)

which may stable and isolatable. The reaction is preferably carried out without isolation of the intermediate of the formula (IIIA) in which case it is reduced in situ to provide a compound of formula (I).

In a typical procedure, an aldehyde of the formula (II) is first reacted with a compound of the formula (III) in a suitable solvent, e.g. tetrahydrofuran, and the mixture then treated with a suitable reducing agent, e.g. sodium triacetoxyborohydride or sodium cyanoborohydride, in the presence of a suitable acid, e.g. acetic acid, to give the required product. If an acid addition salt of a compound of the formula (III) is used as a starting material, a suitable acid acceptor, e.g. triethylamine, can be added prior to the addition of the reducing agent. The reaction is typically carried out at room temperature.

The starting aldehydes or the formula (II) wherein X is $CH_2$ can be prepared by the method shown in the Scheme I and the aldehydes of the formula (II) wherein X is C=O by the method shown in Scheme 2;

SCHEME I

(IV)

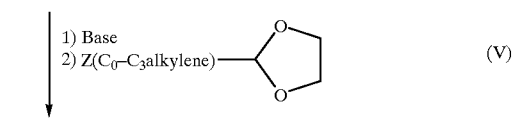

(V)

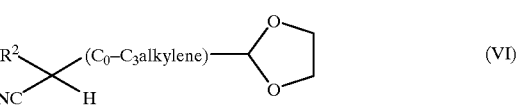

(VI)

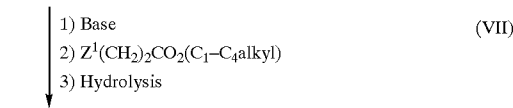

(VII)

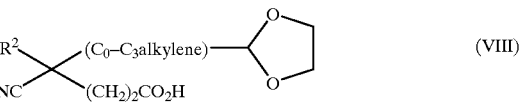

(VIII)

(IX)

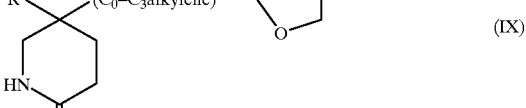

(X)

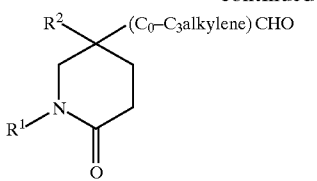

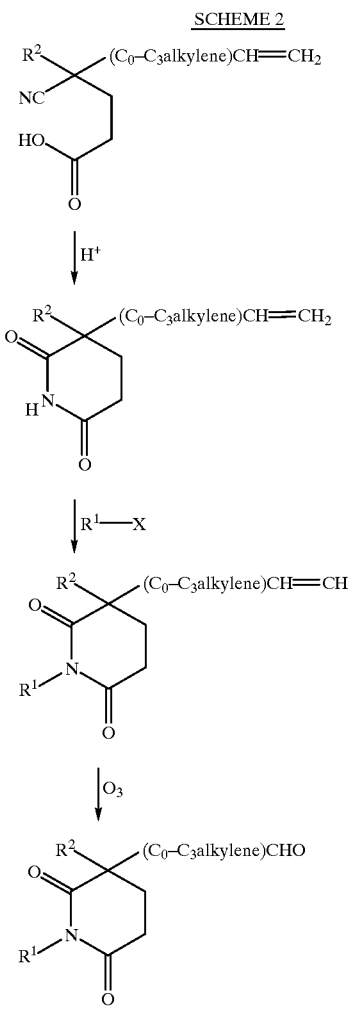

where $R^1$ and $R^2$ are as previously defined for a compound of the formula (I) and Z, $Z^1$ and $Z^2$ are each a suitable leaving group, e.g. chloro, bromo, iodo, methanesulphonyloxy, p-toluenesulphonyloxy or trifluoromethylsulphonyloxy.

In a typical procedure, an arylmethyinitrile of formula (IV) is first deprotonated using a suitable base, e.g. sodium hydride or lithium hexamethyldisilylazide, and then alkylated in situ with an alkylating agent of the formula (V) where Z is preferably bromo. The reaction is typically carried out in a suitable solvent, e.g. tetrahydrofuran, at about 5° C. for the deprotonation and at about room temperature for the alkylation. The acetonitrile derivative of the formula (VI) that is produced is then first deprotonated using a suitable base, e.g. lithium diisopropylamide or lithium hexamethyldisilylazide, and then alkylated in situ with a compound of the formula (VII) where $Z^1$ is preferably bromo. The reaction is typically carried out in a suitable solvent, e.g. tetrahydrofuran, at about 5° C., warming to about room temperature to complete the reaction. Tetra-n-butylammonium iodide can optionally be added following addition of the compound of the formula (VII) to increase the rate of reaction. Finally an aqueous base is added e.g. sodium hydroxide, to produce the carboxylic acid of formula (VIII). The product can be resolved at this stage, if desired, for example by fractional crystallisation of an optically active salt.

The compound of the formula (VIII) prepared is then reduced and cyclised to a pyridone of the formula (IX) under suitable conditions, e.g. using platinum oxide under an atmosphere of hydrogen at atmospheric pressure and room temperature using glacial acetic acid as the solvent.

The pyridone of the formula (IX) is then first deprotonated using a suitable base, e.g. potassium hydride, and then N-alkylated in situ with a compound of the formula $R^1Z^2$ where $Z^2$ is preferably bromo, methanesulphonyloxy or p-toluenesulphonyloxy. The reaction is typically carried out in a suitable solvent, e.g. dimethylsulphoxide, and at about room temperature.

The product of the formula (X) produced is then treated with aqueous hydrochloric acid in a suitable solvent e.g. tetrahydrofuran, to remove the dioxolane protecting group and yield the aldehyde product of formula (II).

Compounds of the formula (II) wherein X is C=O may be prepared in a similar manner by cyclisation of a 4-cyano-4-aryl-hept-6-enoic (XI), prepared as described in WO 96/05193, followed by N-alkylation and ozonolysis of the resulting 3-allyl-glutaramide (XIII).

Preparation of the azabicyclo[3.1.0]hexane starting material of formula (III) wherein $R^3$ is t-butoxycarbonylamino is described in WO93/18001. This may be used as starting material to prepare further intermediates of formula (III) wherein $R^3$ is as defined above. Thus for example the compound is first N-protected by reaction with benzylchloroformate and the t-butoxycarbonyl group removed by treatment with gaseous hydrogen chloride. The resulting 1-benzyloxycarbonyl-1α,5α,6α,6-amino-3-azabicyclo [3.1.0]hexane may then be reacted to introduce various $R^3$ substituent groups. Thus for example reaction with bis-chloroethyl ether and tetra-n-butylbromide by refluxing in dioxan in the presence of sodium hydroxide solution yields 1-benzyloxycarbonyl-1α,5α,6α,6-morpholino-3-azabicyclo [3.1.0]hexane. Removal of the benzyloxycarbonyl group by catalytic hydrogenation yields the compound of formula (III) when $R^3$ is a morpholino group.

As an alternative to the above process, in the case of the compounds of formula (I) wherein $R^3$ is $NH_2$, they may be obtained, for example from the corresponding compound of formula (I) wherein $R^3$ is t-butoxycarbonylamino by deprotection, using for example trifluoroacetic acid. This process may be adapted to use other amino-protected groups present as the $R^3$ substituent and appropriate protecting groups and methods for their removal will be well known to those skilled in the art. This product may be used in turn to prepare further compounds of formula (I). Thus for example in the case of compounds of the formula (I) wherein $R^3$ is —$NR^4SO_2(C_1$–$C_6$ alkyl), —$NR^4SO_2$aryl, —$NR^4CO(C_1$–$C_6$ alkyl) or $NR^4CO$aryl, the compounds may be prepared from the corresponding compound where $R^3$ is $NH_2$ by sulphonylation or acylation with the appropriate sulphonyichloride or acylchloride. Thus for example reaction of the compound of formula (I) wherein $R^3$ is $NH_2$ with a $C_1$–$C_6$alkyl or aryl-sulphonylchloride gives the corresponding compound of formula (I) wherein $R^3$ is NH—$SO_2(C_1$–$C_6$ alkyl) or $NHSO_2$ aryl. The reaction is typically conducted in an organic solvent such as dichloromethane in the presence of an acid acceptor such as triethylamine and is generally complete after several hours at room temperature. Similarly reaction of the amine of formula (I) wherein $R^3$ is $NH_2$ with a $C_1$–$C_6$ acyl or aroylchloride gives the corresponding compounds of formula (I) wherein $R^3$ is $NHCO(C_1$–$C_6$ alkyl) or NHCO aryl. Alkylation of the above products, for example using a $C$–$C_6$ alkyl bromide yields the corresponding compounds wherein $R^4$ is $C_1$–$C_6$alkyl.

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and to the Examples and Preparations hereto.

A pharmaceutically acceptable acid addition or base salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The high activity of the compounds of the invention as neurokinin receptor antagonists is demonstrated by the following procedures:

The affinity of the compounds of formula (I) and their salts for the human $NK_1$ receptor can be tested in vitro by measuring their ability to inhibit [$^3$H]-Substance P binding to membranes prepared from the human IM9 cell line expressing the human $NK_1$ receptor using a modification of the method described in McLean, S. et al, J. Pharm. Exp. Ther., 267, 472–9 (1993) in which, instead of using whole cells, the cells are homogenised using a tissue homogeniser, and the particulate fraction is pelleted by centrifugation and washed three times with buffer prior to resuspension of the membranes.

The affinity of the compounds of formula (I) and their salts for the human $NK_2$ receptor can be measuring in vitro by testing their ability to compete with [$^3$H] or [$^{125}$I]NKA (neurokinin A) for binding to membranes prepared from Chinese hamster ovary cells expressing the cloned human $NK_2$ receptor. In this method, washed Chinese hamster ovary cell membranes are prepared as described for the previous method where IM9 cells are used instead. The membranes are incubated (90 min, 25° C.) with [$^{125}$I] NKA and a range of concentrations of the test compound. Non-specific binding was determined in the presence of 10 $\mu$M NKA.

The $NK_2$ receptor antagonist activity of the compounds of the formula (I) can also be measured, in vitro, by testing their ability to antagonise the contractile effects of the selective $NK_2$ receptor agonist [$\beta$Ala$^8$]NKA$_{(4-10)}$ (Rovereo, P. et al, Neuropeptides, 13, 263–270, 1989) in the rabbit pulmonary artery, using the method of Patacchini and Maggi, Eur. J. Pharmacol., 236, 31–37 (1993).

The compounds of the formula (I) and their salts can be tested for $NK_2$ receptor antagonist activity, in vivo, by measuring their ability to inhibit bronchoconstriction induced by [$\beta$Ala$^8$]NKA$_{4-10)}$ in the anaesthetised guinea pig, using the method described by Murai et al, J. Pharm. Exp. Ther., 262, 403–408 (1992) or Metcalfe et al, Br. J. Pharmacol., 112, 563P (1994).

The compounds of the formula (I) and their salts can be tested for $NK_3$ receptor antagonist activity, in vitro, by measuring their ability to antagonise the contractile effects of the selective $NK_3$ receptor agonist senktide in the guinea-pig ileum using the method of Maggi et al, Br. J. Pharmacol., 101, 996–1000 (1990).

For human use, the compounds of the formula (I) and their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) and their salts will be from 0.001 to 20, preferably from 0.01 to 20, more preferably from 0.5 to 5, and most preferably from 1 to 2, mg/kg (in single or divided doses). Thus tablets or capsules of the compounds will contain from 0.1 to 500, preferably from 50 to 200, mg of active compound for administration singly or two or more at a time, as appropriate. In any event, the physician will determine the actual dosage which will be most suitable for an individual patient and it will vary with the age, weight and response of the particular patient and disease being treated. The above dosages are exemplary of the average case; there can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required. Such formulations will be selected as appropriate to the particular disease being treated and mode of administration required.

It is to be appreciated that reference to treatment includes prophylaxis as well as the alleviation of established symptoms of the disease.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for the treatment of a disease by producing an antagonist effect on a tachykinin acting at the human $NK_1$, $NK_2$ or $NK_3$ receptor, or a combination thereof;

iv) use as in (iii) where the disease is an inflammatory disease such as arthritis, psoriasis, asthma or inflammatory bowel disease, a central nervous system disorder such as anxiety, depression, dementia or psychosis, a gastrointestinal disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain.

v) a method of treatment of a human to treat a disease by producing an antagonist effect on a tachykinin acting at the human $NK_1$, $NK_2$ or $NK_3$ receptor, or a combination thereof, which comprises treating said human with an effective amount of a compound of the formula (I) or with a pharmaceutically acceptable salt or composition thereof;

vi) a method as in (v) where the disease is an inflammatory disease such as arthritis, psoriasis, asthma or inflammatory bowel disease, a central nervous system disorder such as anxiety, depression, dementia or psychosis, a gastrointestinal disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain;

The following Examples illustrate the preparation of the compounds of the formula (I):

EXAMPLE 1

5(S)-5-(3,4-Dichlorophenyl)-1-(cyclopropylmethyl-5-(2-[1α,5α,6α-6-morpholino-3-azabicyclo[3.1.0]hexane]ethyl)-2-piperidone A solution of 5(S)-1-cyclopropylmethyl-5-(3,4-dichlorophenyl)-5-formylmethyl-2-piperidone (130 mg, 0.38 mmol) (see preparation 5) and 1α,5α,6α-6-morpholino-3-azabicyclo[3.1.0]hexane (see preparation 4) in tetrahydrofuran was stirred for 30 minutes at room temperature. Sodium triacetoxyborohydride (120 mg, 1.5 mol equivalents) and glacial acetic acid (0.021 ml) were added and the mixture stirred for one hour. Water (1 ml) was added followed by saturated sodium carbonate solution (10 ml) and the mixture extracted with ethyl acetate (3×20 ml). The combined organic extracts were dried over magnesium sulphate, filtered, and the solvent removed from the filtrate under reduced pressure. The residue was chromatographed on silica gel eluting with a solvent gradient of methanol to methylene chloride (5:95, 10:90), to give the title compound (100 mg). TLC $R_F$=0.3 (silica, methanol:dichloromethane 10:90 by volume). LRMS m/z=492 (m+1)⁺. Found: C,60.68; H,6.91; N,7.97. $C_{26}H_{35}Cl_2N_3O_2$. 0.33 $CH_2Cl_2$ requires C,60.70; H,6.91; N,8.07%. ¹H-NMR (CDCl₃) δ=0.2–0.4(m, 2H), 0.5–0.7(m,2H), 1.0–1.05(m,1H), 1.4(s,2H), 1.6(s,2H), 1.7–1.9(m,2H), 2.0–2.2(m,6H), 2.3–2.49(m,1H), 2.5(m, 4H), 2.8–2.9(dd,2H), 3.2(m,1H), 3.4–3.5(m,2H), 3.665(m, 4H), 3.8(d,1H), 7.1(dd,1H), 7.4(m,2H)ppm.

EXAMPLE 2

5(S)-5-(3,4-Dichlorophenyl)-1-(cyclopropylmethyl)-5-(2-[1α,5α,6α-6-t-3-azabicyclo[3.1.0]hexane]ethyl)-2-piperidone A solution of 5(S)-1-cyclopropylmethyl-5-(3,4-dichlorophenyl)-5-formylmethyl-2-piperidone (1.5 g, 4.41 mmol) (see preparation 5) and 1α,5α,6α-6-t-butoxycarbonylamino-3-azabicyclo[3.1.0]hexane (see preparation 4) in tetrahydrofuran was stirred for 40 minutes at room temperature. Sodium triacetoxyborohydride (1.4 g, 1.5 mol equivalents) and glacial acetic acid (0.24 ml) were added and the mixture stirred for eighteen hours. Saturated sodium carbonate solution (20 ml) was added and the mixture extracted with ethyl acetate (3×40 ml). The combined organic extracts were dried over magnesium sulphate, filtered, and the solvent removed from the filtrate under reduced pressure. The residue was chromatographed on silica gel eluting with a solvent gradient of methanol to ethyl acetate (5:95, 10:90), to give the title compound (1.1 g). TLC $R_F$=0.1–0.2 (silica, ethyl acetate:methanol, 90:10 by volume). LRMS m/z=522 (m=1)⁺. Found: C,61.74; H,7.47; N,7.99. $C_{27}H_{37}Cl_2N_3O_3$ requires C, 62.05; H,7.14; N,8.04%. ¹H-NMR(CDCl₃) δ=0.2–0.4(m,2H), 0.5 –0.7(m, 2H), 1.0–1.05(m,1H), 1.3(m,1H), 1,4(s,9H), 1.7(m,1H), 1.9 (m,1H), 2.0–2.2(m,8H), 2.3–2.35(m, 1H), 2.65(s, 1H), 2.9–3.0(dd,2H), 3.1–3.2(m,1H), 3.4–3.5(m,2H),3,8(d,1H), 4.4–4.6(s,br,1H), 7.1(dd,1H), 7.4(m,2H) ppm.

EXAMPLE 3

5(S)-5-(3,4-Dichlorophenyl)-1-(cyclpropylmethyl)-5-(2-[1α,5α,6α-6-amino-3-azabicyclo[3.1.0]hexane]ethyl)-2-piperidone di-trifluoroacetate salt To a solution of the compound from example 2, (1.0 g, 1.92 mmol), in methylene chloride was added trifluoroacetic acid (2.2 ml, 15 mol equivalents) with ice bath cooling. The reaction was allowed to warm to room temperature overnight. The reaction mixture was evaporated under reduced pressure and then re-evaporated from methylene chloride and then diethyl ether, to give a gum, 1.2 g. TLC $R_F$=0.2 (silica, methylene chloride;methanol, 90:10 by volume). LRMS m/z=422(M+1)⁺. ¹H-NMR(CDCl₃) δ=0.2–0.4(m, 2H), 0.5–0.6(m,2H), 0.95–1.05(m,1H), 1.8–2.3(m,10H), 2.6–2.8(m,3H), 3.0–3.3(m,3H), 3.4–3.8(m,3H), 7.47(d, 1H), 7.6(m,2H), 8.3(s,br,3H), 10(s,broad,0.5H), 10.5(s,broad, 0.5H) ppm.

EXAMPLE 4

5(S)-5-(3,4-Dichlorophenyl)-1-(cyclopropylmethyl)-5-(2-[1α,5α,6α-6-amino-3-azabicyclo[3.1.0]hexane]ethyl)-2-piperidone The compound from example 3 (400 mg) was dissolved in methylene chloride and washed with sodium hydrogen carbonate solution. The organic layer was separated, dried over magnesium sulphate, filtered under reduced pressure and evaporated under reduced pressure to give a gum. This was chromatographed on silica eluting with a solvent gradient of methylene chloride to methanol (95:5, 90:10) to give the title compound (200 mg). TLC $R_F$=0.1 (silica, methylene chloride:methanol, 90:10 by volume). LRMS m/z=422(M+1)⁺. Found: C,59.27; H,6.47; N,9.58. $C_{22}H_{29}Cl_2N_3O$ 0.25 $CH_2Cl_2$ requires C,59.54; H,6.70; N,9.47%. ¹H-NMR (CDCl₃) δ=0.2–0.4(m,2H), 0.5–0.7(m, 2H), 1.0–1.1(m,1H), 1.3(s,2H), 1.4–1.7(br,s,3H), 1.7–1.8(m, 1H), 1.8–1.9(m,1H), 1.9–2.2(m,6H), 2.5–2.7(m,2H), 2.8–3.0(m,2H), 3.1–3.2(m,1H), 3.4–3.5(m,2H), 3.7–3.9(m, 1H), 7.1–7.2(m,1H), 7.4(m,2H) ppm.

EXAMPLE 5

5(S)-5-(3,4-Dichlorophenyl)-1-(cyclopropylmethyl)-5-(2-[1α,5α,6α-6-methanesulphonylamino-3-azabicyclo[3.1.0]hexane]ethyl)-2-piperidone To a solution of the compound from example 3 (450 mg, 0.69 mmol) and triethylamine (0.45 ml, 4.5 mole equivalents) in methylene chloride (15 ml) was added methanesulphonyl chloride (0.1 ml, 2 mol equivalents). The mixture was stirred for thirty minutes and stood at room temperature overnight. The reaction mixture was diluted with methylene chloride and washed with water (15 ml). The organic layer was dried over magnesium sulphate, filtered under reduced pressure and the solvent removed under reduced pressure to give a gum. This was chromatographed on silica eluting with solvent gradient of ethyl acetate to methanol, (90:10, 80:20) to give the title compound as a foam (95 mg) after re-evaporation from diethyl ether. TLC $R_F$=0.5 (silica, methylene chloride:methanol, 90:10 by volume). LRMS m/z=500(M+1)$^+$. Found: C,54.23; H,6.04; N, 8.13. $C_{23}H_{31}Cl_2N_3O_3S$. 0.5 $H_2O$ requires C,54.21; H,6.33; N,8.25%. $^1$H-NMR (CDCl$_3$) δ=0.4–0.6(m,2H), 0.5–0.7(m,2H), 1.0–1.1(m,1H), 1.7(s,3H), 1.8–2.4(m,9H), 2.7(br,s,2H), 3.0(s,4H), 3.1–3.2(m,1H), 3.4–3.5(m,2H), 3.75 (d,1H), 4.5(s,1H), 7.1(m,1H), 7.35–7.45(m,2H) ppm.

EXAMPLE 6

5(S )-5-(3,4-Dichlorophenyl)-1-(cyclopropylmethyl)-5-(2-[1α,5α,6α-6-Pentafluorophenylsulphonylamino-3-azabicyclo[3.1.0]hexane]ethyl)-2-piperidone To a solution of the compound from example 3 (1.0 g, 1.53 mmol) and triethylamine (0.68 ml, 3.2 mole equivalents) in methylene chloride (15 ml) was added pentafluorophenylsulphonyl chloride (0.49 g, 1.2 mol equivalents). The mixture was stirred for thirty minutes and stood at room temperature overnight. The reaction mixture was diluted with methylene chloride and washed with water (15 ml). The organic layer was dried over magnesium sulphate, filtered under reduced pressure and the solvent removed under pressure to give a gum. This was chromatographed on silica eluting with solvent gradient of ethyl acetate to methanol, (90:10, 80:20). The compound was triturated with ethyl acetate and diethyl ether and the white solid obtained filtered and discarded. The filtrate was evaporated and rechromatographed on silica eluting with a solvent gradient of methylene chloride to methanol 90:10. LRMS m/z=652(M+1)$^+$. Found: C,51.83; H,4.24; N,6.32. $C_{28}H_{28}Cl_2F_5N_3O_3S$ requires C,51.53; H,4.32; N,6.44%. $^1$H-NMR (CDCl$_3$) δ=0.4–0.6(m,2H), 0.5–0.7(m,2H), 1.0–1.1(m,1H), 1.5(s,2H), 1.6–1.9(m,2H), 1.9–2.2(m,8H ), 2.3–2.4(m,1H), 2.5(s,1H), 2.9(m,2H), 3.35–3.5(m, 2H), 3.75(d,1H), 5.3(d,1H),7.1(m,1H), 7.35–7.45(m,2H) ppm.

EXAMPLE 7

5(S)-5-(3,4-Dichlorophenyl)-1-(cyclopropylmethyl)-5-(2-[1α,5α,6α-6-4'-fluorophenylsulphonylamino-3-azabicyclo[3.1.0]hexane]ethyl)-2-piperidone To a solution of the compound from example 3 (1.0 g, 1.53 mmol) and triethylamine (0.86 ml, 4 mole equivalents) in methylene chloride (15 ml) was added 4-fluorophenylsulphonyl chloride (0.36 g, 1.2 mol equivalents). The mixture was stirred at room temperature for five hours and stood at room temperature overnight. The reaction mixture was diluted with methylene chloride and washed with water (2×20 ml). The organic layer was dried over magnesium sulphate, filtered under reduced pressure and the solvent removed under reduced pressure to give a gum. This was chromatographed on silica eluting with solvent gradient of methylene chloride to methanol, (95:5, 92:8) to give the title compound as a gum (140 mg). TLC $R_F$=0.5 (silica, methylene chloride:methanol, 90:10 by volume). LRMS m/z=580(M+1)$^+$. Found: C,57.17; H,5.56; N,7.09. $C_{28}H_{32}FCl_2N_3O_3S$. 0.25 $H_2O$ requires C,57.47; H,5.60; N,7.18%. $^1$H-NMR (CDCl$_3$) δ=0.4–0.6(m,2H), 0.5–0.7(m,2H), 1.0–1.1(m,1H), 1.7(s,3H), 1.6–2.0(m,1H), 2.0–2.25(m,7H), 2.3–2.4(m,2H), 2.8–2.9(m,2H), 3.0–3.2(m, 1H), 3.4–3.6(m,2H), 3.7(d,1H), 4.6(s,1H), 7.1(m,1H), 7.2–7.3(m,2H), 7.35–7.45(m,2H), 7.85–7.95(m,2H) ppm.

EXAMPLE 8

5(S)-5-(3,4-Dichlorophenyl)-1-cyclopropylmethyl)-5-(2-[1α,5α,6α-6-4'-fluorophenylcarboxyamido-3-azabicyclo[3.1.0]hexane]ethyl)-2-piperidone trifluoroacetate salt To a solution of the compound from example 3 (300 mg, 0.46 mmol) and triethylamine (0.26 ml, 4 mole equivalents) in methylene chloride (15 ml) was added 4-fluorobenzoyl chloride (0.07 ml, 1.2 mol equivalents). The mixture was stirred at room temperature overnight. The reaction mixture was diluted with methylene chloride and washed with water (2×20 ml). The organic layer was dried over magnesium sulphate, filtered under reduced pressure and the solvent removed under reduced pressure to give a gum. This was chromatographed on silica eluting with solvent gradient of ethyl acetate to methanol, (90:10, 80:20) to give the title compound as a gum (100 mg). TLC $R_F$=0.1–0.2(silica, ethyl acetate:methanol, 90:10 by volume). LRMS m/z=544 (M+1)$^+$. Found: C,56.06; H,4.83; N,5.99. $C_{29}H_{32}FCl_2N_3O_2$ monotrifluoroacetate salt. 0.02 ethyl acetate requires C,55.76; H,4.71; N,6.22%. $^1$H-NMR (CDCl$_3$) δ=0.2–0.3(m, 2H), 0.4–0.5(m,2H), 0.9–1.1(m,1H), 1.5(s,2H), 1.6–1.9(m, 3H), 1.9–2.1(m,1H), 2.1–2.3(m,6H), 2.85–3.0(m,3H), 3.1–3.2(m,$_1$H), 3.5(d,2H), 3.8(d,$_1$H), 7.1–7.3(m,2H), 7–7.4 (m,1H), 7.5–7.7(m,2H), 7.85–7.9(m,2H), 8.3(d,1H) ppm.

EXAMPLE 9

5-(3 4-Dichlorophenyl)-1-benzyl-5-(2-[1α,5α,6α-6-morpholino-3-azabicyclo[3.1.0]hexane]ethyl)-2-piperidone A solution of 1-benzyl-5-(3,4-dichlorophenyl)-5-formylmethyl-2-piperidone (0.28 g, 0.75 mmol) (see preparation 6) and 1α,5α,6α-6-morpholino-3-azabicyclo[3.1.0] hexane (0.14 g, 0.83 mmol) (see preparation 4) in tetrahydrofuran was stirred for 45 minutes. Sodium triacetoxyborohydride (245 mg, 1.5 mol equivalents) and glacial acetic acid (0.045 ml) were added and the mixture stirred for one hour. Saturated sodium carbonate solution (10 ml) was added and the mixture extracted with ethyl acetate (3×20 ml). The combined organic extracts were dried over magnesium sulphate, filtered, and the solvent removed from the filtrate under reduced pressure. The residue was chromatographed on silica gel eluting with a solvent gradient of methanol to methylene chloride (2:98, 5:95, 10:90), to give the title compound (235 mg). TLC $R_F$=0.3 (silica, methanol:dichloromethane 10:90 by volume). Found: C,66.14; H,6.88; N,7.81. $C_{29}H_{35}Cl_2N_3O_2$ requires C,65.89; H,6.67; N,7.95%. $^1$H-NMR (CDCl$_3$) δ=1.4 (s,2H), 1.5–1.8(m,2H), 1.9–2.1(m,4H), 2.1–2.25(m,4H), 2.3–2.4(m,1H), 2.5–2.6(m, 4H), 2.7–2.9(m,2H), 3.3(d,1H), 3.5–3.6(d,1H), 3.6–3.7(m, 4H), 4.35(d,1H), 4.85(d,1H), 6.8(m,1H), 7.1(m,1H), 7.2–7.5 (m,6H) ppm.

EXAMPLE 10

3(S)-1-Cyclopropylmethyl-3-(3,4-dichlorophenyl)-3-(2-[1α,5α,6α-6-morpholino-3-azabicyclo[3.1.0]hexane]ethyl)glutarimide The procedure of Example 1 was followed starting with 3(S)-1-cycloproplymethyl-3-(3,4-dichlorophenyl)-3- formylmethyl-glutarimide (see preparation 7) to yield the title compound as a gum. Found: C,60.71; H,6.24; N,7.20. $C_{26}H_{33}Cl_2N_3O_3$. 0.5 $H_2O$ requires C,60.58; H,6.64; N,8.15%. $^1$H NMR ($CDCl_3$): 0.25–0.55(m,4H), 1.1–1.3(m, H), 1.5–1.6(m,8H), 1.8–2.0)(m,2H), 2.1–2.7(m,11H), 2.9–3.0(m,2H), 3.6–3.65(m,4H), 3.7–3.8(m,2H), 7.0–7.05 (m,1H), 7.35–7.4(m,2H).

Preparation 1

1-Benzyloxycarbonyl-1α,5α,6α-6-t-butoxycarbonylamino-3-azabicyclo[3.1.0]hexane

Benzylchioroformate (1.10 ml, 7.8 mmol) was added to an ice-cooled solution of 1α,5α,6α-6-t-butoxycarbonylamino-3-azabicyclo[3.1.0]hexane (1.4 g, 7.1 mmol) (prepared as described in WO93/18001) and triethylamine (1.1 ml, 7.8 mmol) in dichloromethane (35 ml). The reaction was stirred for one hour and then water was added, the organic layer was washed with water, dried over magnesium sulphate, filtered and the solvent removed under reduced pressure to give the title compound as a gum (3.0 g). TLC $R_F$=0.6 (silica, methanol: dichloromethane 5:95 by volume). LRMS m/z=350($MNH_4$)$^+$. $^1$H-NMR ($CDCl_3$) δ=1.4(s,9H), 1.7(s,2H), 2.3(s,1H), 3.5(m,2H), 3.7(m,2H), 4.6(m,1H), 5.1(s,2H), 7.

Preparation 2

1-Benzyloxycarbonyl-1α,5α,6α-6-amino-3-azabicyclo[3.1.0]hexane

Hydrogen chloride gas was bubbled through a solution of the compound from preparation 1 (3.0 g) in ethyl acetate (40 ml) with ice-cooling. After one hour the ethyl acetate was evaporated and the residue partitioned between methylene chloride and 10% sodium carbonate solution. The organic layer was dried over magnesium sulphate, filtered, and the solvent removed under reduced pressure to give an oil, (1.4 g). TLC $R_F$=0.3 (silica, methanol:dichloromethane 5:95 by volume). $^1$H-NMR ($CDCl_3$) δ=1.7(s,1H), 1.9(s,3H), 2.1(s, 1H), 3.4–3.8(m,4H), 5.1(m,2H), 7.3(m,5H) ppm.

Preparation 3

1-Benzyloxycarbonyl-1α,5α,6α,6-morpholino-3-azabicyclo[3.1.0]hexane

The compound from preparation 2 (1.4 g, 6.03 mmol), bis-chloroethylether (1.1 ml, 9.1 mmol), and tetra-n-butylbromide (200 mg) were refluxed together in a solution of dioxan (30 ml) and 2N sodium hydroxide solution for 18 hours. After this time further bis-chloroethyl ether (1.1 ml) was added reflux continued for a further 18 hours followed by the addition of a further portion of bis-chloroethylether (1.1 ml) and further reflux for 18 hours. The dioxan was evaporated under reduced pressure and the residue partitioned between methylene chloride and water. The organic layer was separated, dried over magnesium sulphate, filtered and the solvent removed under reduced pressure. The residue was chromatographed on silica using a gradient elution of methylene chloride to methanol (98:2, 95:5), to give the product fractions as an oil which crystallised on standing. (0.68 g). TLC $R_F$=0.5 (silica, methanol:dichloromethane 5:95 by volume). LRMS m/z=303 (m+1)$^+$. $^1$H-NMR($CDC_3$) δ=1.5(s,1H), 1.8(m,2H), 2.5–2.6(m,3H), 3.4–3.5(m,2H) 3.5–3.7(m,7H), 5.1(s,2H),7.3(m,5H) ppm.

Preparation 4

1α,5α,6α,6-morpholino-3-azabicyclo[3.1.0]hexane

A solution of the compound from preparation 3 (0.65 g, 2.1 mmol) in ethanol (50 ml) was added to 5% palladium on carbon (300 mg) and the mixture stirred under an atmosphere of hydrogen at 345 kPa (50 psi) and at room temperature for 18 hours. The catalyst was removed by filtration and the solvent removed under reduced pressure to give an oil (0.35 9) which crystallised on standing overnight. $^1$H-NMR($CDCl_3$) δ=1.5–1.6(m,3H), 2.2–2.4(br,s,1H), 2.5–2.6(m,4H), 2.9–3.1 (m,4H),3.6–3.8(m,4H).

Preparation 5

5(S)-1-Cyclopropylmethyl-5-(3,4-dichlorophenyl)-5-formylmethyl-2-piperidone (a) 4(S)-4-Cyano4-(3,4-dichlorophenyl)-5-(1,3-dioxolan-2-yl)entan-1-oic acid To a 1.0 M solution of lithium hexamethyidisilylazide in tetrahydrofuran 4.69 l) at 5° C. under nitrogen was added a solution of 3,4 dichlorophenylacetonitrile (750 g, 4.28 moles) in tetrahydrofuran (750 ml), dropwise, over 45 minutes. The reaction was allowed to stir for 2 hours.

The reaction was cooled again to 5° C. and a solution of 2-bromomethyl-1,3-dioxolane (782 g) in tetrahydrofuran (780 ml) added, dropwise, over fifty minutes. Tetra-n-butylammonium iodide (75 g) was added, portionwise, and the mixture allowed to warm to room temperature and stirred for 14 hours. The reaction was then cooled to 5° C. and a 1.0M solution of lithium hexamethyidisilylazide in tetrahydrofuran (4.69 l) was added, dropwise. The mixture was stirred for 5 hours at room temperature. The solution was cooled to 5° C. and a solution of ethyl 3-bromopropanoate (840.5 g) in tetrahydrofuran (840 ml) was added, dropwise, over 50 minutes. The reaction was allowed to stir for 14 hours. The reaction mixture was cooled to 5° C. and 1.5M aqueous sodium hydroxide solution (containing 255 g of sodium hydroxide) was added and the mixture stirred for 14 hours. Water (5 l) was added and the mixture was extracted with ethyl acetate (2×l). The combined organic extracts were washed with water (2×5 l). The aqueous phases were combined and acidified to pH1 using 5N aqueous hydrochloric acid solution and then extracted with ethyl acetate (2×3 l). The combined organic extracts were concentrated under reduced pressure to a concentration of approximately 3 ml/g based on the theoretical yield of the product.

The above experimental procedure was then repeated on an identical scale. To the combined organic solutions from both reactions was added (S)-(–)-alpha-methylbenzylamine (1.13 kg) and the mixture stirred for 14 hours. The thick slurry was then stirred with cooling in an ice-bath for 2 hours, filtered, the solid washed with ethyl acetate (2×1 l) and then dried under reduced pressure at 35° C. to give 1.85 kg of material. A portion of this material (1.34 kg) was dissolved in a mixture of butanone (2 l) and water (503 ml) that was heated under reflux. A further portion of butanone (4.7 l) was added and the solution was allowed to cool slowly to room temperature overnight. The resulting solid was filtered, washed with butanone (2×l) and dried under reduced pressure at 35° C. for 10 hours to give 563 g of material (93.8%). A further recrystallisation from butanone/water gave the title compound as a (S)-(–)-alpha-methylbenzylamine salt in 99.8% yield. To a stirred solution of this salt in ethyl acetate and water was added 5N aqueous hydrochloric solution until pH1 was achieved. The mixture was stirred for a further 30 minutes, the layers separated and the aqueous phase extracted with ethyl acetate. The combined organic layers were washed with water and the solvent removed by evaporation under reduced pressure to give the title compound.

$^1$H-NMR ($CDCl_3$): δ=2.05–2.35(m,4H), 2.4–2.65(m,2H), 3.7–4.0(m,4H), 4.75–4.85(m,1H), 7.25–7.55(m,3H), 9.9(s, br.,1H,acid) ppm.

(b) 5(S)-5-(3,4-Dichlorophenyl)-5-(1,3-dioxolan-2-ymethyl)-2(1H)-piperidone

To a solution of the above compound (13.5 g, 39.22 mmol) in glacial acetic acid (130 ml) was added platinum oxide (1.21 g) and the mixture stirred under an atmosphere of hydrogen at 414 kPa (60 psi) and at room temperature for 17 hours. The catalyst was removed by filtration and a further portion of platinum oxide (1.21 g) added. The reaction mixture was then stirred under an atmosphere of hydrogen 414 kPa (60 psi) and at room temperature for 48 hours. The catalyst was removed by filtration and the solution concentrated under reduced pressure. The residue was dissolved in ethyl acetate (80 ml) and washed with saturated aqueous sodium bicarbonate solution (2×75 ml). The organic phase was then separated and the solvent removed under reduced pressure. The resulting solid was stirred in a solution of hexane (20 ml) and ethyl acetate (20 ml) for 2 hours at 0° C. and then filtered off to give the title compound (8.15 g).

$^1$H-NMR (CDCl$_3$): δ=1.85–1.95(m,1H), 2.0–2.25(m,4H), 2.35–2.4(m,1H), 3.45–3.55(m, 1H), 3.65–3.75(m,2H), 3.8–3.9(m,3H), 4.35–4.4(m,1H), 6.15(s,br.,1H), 7.2–7.45 (m,3H) ppm.

(c) 5(S)-1-Cyclpropylmethyl-5-(3,4-dichlororhenyl)-5-(1,3-dioxolan-2-ylmethyl)-2-piperidone To a solution of the above compound (38.6 g, 117 mmol) in dimethyl sulphoxide (190 ml) was added potassium hydroxide (19.7 g) and the mixture stirred at room temperature for 20 minutes. Bromomethylcyclopropane (17.37 g ) was then added over 20 minutes and the reaction stirred for a further 140 minutes. The reaction was poured into a mixture of ice (100 g) and water (900 ml) and the mixture extracted with dichloromethane (2×400 ml). The combined organic layers were washed with water (400 ml) and the solvent removed under reduced pressure to give the title compound (45.4 g).

$^1$H-NMR (CDCl$_3$): δ=0.3–0.4(m,2H), 0.55–0.65(m,2H), 1.05–1.15(m,1H),1.9–1.95(m, 1H), 2.0–2.25(m,4H), 2.35–2.45(m,1H), 3.1 5–3.2(m,1H), 3.5–3.55(m,2H), 3.65–3.75(m,2H), 3.9–4.0(m,3H), 4.35–4.4(m, 1H), 7.2–7.5 (m,3H) ppm.

(d) 5(S)-1-Cyclopropylmethyl-5-(3,4-dichlorophenyl)-5-formyl methyl-2-piperidone To a solution of the above compound of (73.16 g, 190 mmol) in tetrahydrofuran (730 ml) at 5° C. was added 5N aqueous hydrochloric acid solution (730 ml) over 20 minutes. The reaction mixture was stirred at room temperature for 17 hours. The tetrahydrofuran was removed under reduced pressure, the residue diluted with water (200 ml) and extracted with ethyl acetate (2×500 ml). The combined organic layers were then washed with water (500 ml) and the solvent removed under reduced pressure to give the title compound (62.1 g).

$^1$H-NMR (CDCl$_3$): δ=0.25–0.35(m,2H), 0.55–0.65(m, 2H), 1.05–1.1(m, 1H), 2.15–2.25(m,3H), 2.35–2.5(m,1H), 2.65–2.75(m,1H), 2.95–3.05(m,1H), 3.15–3.2(m,1H), 3.45–3.6(m,2H), 3.95–4.0(m,1H), 7.2–7.45(m,3H), 9.5(s, 1H) ppm.

Preparation 6

1-Benzyl-5-(3,4-dichlorophenyl)-5-formylmethyl-2-piperidone

The procedure of preparation 5 was followed using benzylbromide in step (c) instead of bromomethylcyclopropane and omitting the salt resolution in step (a), to give the title compound as a gum. LRMS m/z=376(m+1)$^+$. $^1$H-NMR δ=2.1–2.3(m,3H), 2.4–2.55(m,2H), 2.6(dd,,1H), 2.85(dd, 1H), 3.4(d, 1H), 3.75(d, 1H), 4.45, (d, 1H), 4.8(d, 1H), 6.85(m, 1H), 7.25–7.4(m, 7H) ppm.

Preparation 7

3(S)-1-Cyclopropylmethyl-3-(3,4-dichlorophenyl)-3-formylmethyl-glutarimide (a) 3(S)-3-Allyl-3-(3,4-dichlorophenyl)-(1H)glutarimide A solution of 4(S)-4-Cyano-4-(3,4-dichlorophenyl)hept-6-enoic acid (3.4 g, 11.4 mmol), formic acid (4 ml), and hydrochloric acid (2 ml) in dimethylformamide (23 ml) was heated at 145° C. for 48 hours. The solution was cooled to room temperature and water (50 ml) added. The mixture was basified using 15% aqueous sodium carbonate solution until an oily precipitate formed and then extracted with ethyl acetate (2×50 ml). The combined organic phases were dried over anhydrous sodium sulphate, filtered and the solvent removed under reduced pressure to give an oil which was purified by flash column chromatography on silica gel using hexane:ethyl acetate (3:1, by volume) as eluant to give the title compound (1.62 g). TLC Rf=0.87 (silica, ethyl acetate-:hexane 1:3, by volume). m.p.=137–138° C. [α]$^{25}_{589}$=178° (c=0.00034).

(b) 3(S)-3-Allyl-1-cyclopropylmethyl-3-(3,4-dichlorophenyl)glutarimide

The above product (0.77 g, 2.59 mmol) was reacted with bromomethyl-cyclopropane (276 μl 1.1 mol. equiv.) following the procedure of Preparation 5(c) to yield the 1-cyclopropylmethyl derivative (0.68 g). LRMS m/z=352 (M+1)$^+$. TLC Rf 0.47 (silica, diethylether;hexane 1:1 by volume).

(c) 3(S)-1-Cyclopropyl methyl-3-(3,4-dichlorophenyl)-3-formylmethyl-glutarimide

Into a solution of the above compound (717 mg, 1.82 mmol) in methanol (40 ml) under nitrogen at −78° C. was bubbled ozone at a rate of 50 ml/min (using a charge of 1.5A to generate ozone from oxygen) for twenty minutes. After this time the amperage was reduced to zero and oxygen bubbled through the reaction at a rate of 5 ml/min for ten minutes. The oxygen supply was then removed and a solution of dimethylsulphide (1.33 ml) in methanol (5 ml) was added dropwise and the reaction left to warm to room temperature for eighteen hours. The solvent was removed under reduced pressure and the reaction mixture partitioned between ethyl acetate (30 ml) and water (30 ml). The organic layer was dried over anhydrous magnesium sulphate, filtered and the solvent removed under reduced pressure to give the title compound (630 mg) which was used without further purification. TLC Rf=0.18 (silica, diethyl ether:hexane 1:1 by volume). LRMS m/z=354 (M+1).

We claim:

1. A compound having the formula:

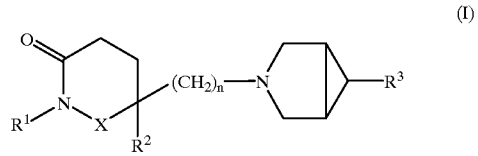

(I)

or a pharmaceutically acceptable salt thereof, wherein:
R$^1$ is C$_1$–C$_6$ alkyl, C$_3$–C$_7$ cycloalkyl, C$_3$–C$_7$ cycloalkyl (C$_1$–C$_4$)alkyl, aryl or aryl-(C$_1$–C$_4$)alkyl; wherein the C$_1$–C$_6$ alkyl group is optionally substituted by one or more fluorine atoms and the C$_3$–C$_7$ cycloalkyl or C$_3$–C$_7$ cycloalkyl(C$_1$–C$_4$)alkyl group is optionally substituted in the cycloalkyl ring by up to two substituents each independently selected from halo, $C_1$–$C_4$ alkoxy or halo($C_1$–$C_4$)alkoxy;

$R^2$ is phenyl optionally substituted with one or two halo substituents or is indolyl, thienyl, benzothienyl, or naphthyl;

$R^3$ is $NH_2$, —$NR^4SO_2$($C_1$–$C_6$ alkyl), —$NR^4SO_2$ aryl, —$NR^4SO_2N(R^4)_2$, —$NR^4CO$($C_1$–$C_6$ alkyl), —$NR^4CO$ aryl or a group of the formula:

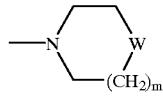

wherein W is O, $NR^5$, CH(OH), $CHCO_2H$, $CHN(R^4)_2$, CHF, $CF_2$, C=O or $CH_2$;

$R^4$ is H or $C_1$–$C_6$ alkyl;

$R^5$ is H, $C_1$–$C_6$ alkyl, $C_3$–$C_7$ cycloalkyl, $C_3$–$C_7$ cycloalkyl ($C_1$–$C_6$)alkyl, $C_2$–$C_6$ alkanoyl, $C_4$–$C_8$ cycloalkanoyl, $C_3$–$C_7$ cycloalkyl($C_2$–$C_6$)alkanoyl, aryl CO—, $C_1$–$C_6$ alkyl $SO_2$—, $(R^4)_2NSO_2$—, $C_3$–$C_7$ cycloalkyl $SO_2$—, $C_3$–$C_7$ cycloalkyl($C_1$–$C_6$)-alkyl $SO_2$— or aryl $SO_2$—;

X is $CH_2$ or C=O;

m is 0, 1 or 2 with the proviso that m is not 0 when W is $NR^5$, C=O, or O; and n is an integer of from 1 to 4.

2. A compound as claimed in claim 1 wherein X is $CH_2$ and $R^1$ is cyclopropylmethyl or benzyl.

3. A compound as claimed in claim 1 wherein $R^2$ is 3,4-dichlorophenyl.

4. A compound as claimed in claim 1 wherein n is 2.

5. A compound as claimed in claim 1 wherein $R^3$ is morpholino, methanesulphonylamino, pentafluorophenylsulphonylamino, fluorophenylsulphonylamino, or fluorophenylcarboxamido.

6. The compound 5(S)-5-(3,4-dichlorophenyl)-1-(cyclopropylmethyl)-5-(2-[1α,5α,6α,6-morpholino-3-azabicyclo[3.1.0]hexane]ethyl)-2-piperidone.

7. A pharmaceutical composition comprising a compound of the formula (I) as claimed in claim 1, or a pharmaceutically acceptable salt thereof, together with a pharmaceutically acceptable diluent or carrier.

8. A method for treating urinary incontinence and asthma in a human subject, which comprises the step of administering to said subject in need of such treatment, a therapeutically effective amount of a compound of claim 1.

* * * * *